(12) United States Patent
Kamei

(10) Patent No.: US 9,332,986 B2
(45) Date of Patent: May 10, 2016

(54) MEDICAL STAPLER

(75) Inventor: Toshiharu Kamei, Utsunomiya (JP)

(73) Assignee: Mani, Inc. (JP)

( * ) Notice: Subject to any disclaimer, the term of this patent is extended or adjusted under 35 U.S.C. 154(b) by 592 days.

(21) Appl. No.: 13/634,243

(22) PCT Filed: Mar. 30, 2011

(86) PCT No.: PCT/JP2011/057941
§ 371 (c)(1),
(2), (4) Date: Sep. 12, 2012

(87) PCT Pub. No.: WO2011/125693
PCT Pub. Date: Oct. 13, 2011

(65) Prior Publication Data
US 2013/0001271 A1 Jan. 3, 2013

(30) Foreign Application Priority Data

Mar. 31, 2010 (JP) ................... 2010-081419

(51) Int. Cl.
A61B 17/04 (2006.01)
A61B 17/10 (2006.01)
A61B 17/068 (2006.01)
A61B 17/072 (2006.01)

(52) U.S. Cl.
CPC ........... *A61B 17/0684* (2013.01); *A61B 17/068* (2013.01); *A61B 2017/07271* (2013.01)

(58) Field of Classification Search
CPC ........... A61B 2017/07271; A61B 2017/07278; A61B 2017/0053; A61B 17/068

USPC ........................................... 227/175.1–182.1
See application file for complete search history.

(56) References Cited

U.S. PATENT DOCUMENTS 4,179,057 A * 12/1979 Becht ................. A61B 17/0684
227/120
4,558,810 A * 12/1985 Mulhauser ......... A61B 17/0684
227/19

(Continued)

FOREIGN PATENT DOCUMENTS

JP S57-125743 A 8/1982
JP 2006-305136 A 11/2006
WO WO 03099135 A1 * 12/2003 ......... A61B 17/0684

*Primary Examiner* — Robert Long
(74) *Attorney, Agent, or Firm* — Lerner, David, Littenberg, Krumholz & Mentlik, LLP

(57) ABSTRACT

A medical stapler according to the present invention includes a magazine containing staples, a rail for aligning the staples, and a mechanism for punching out staples; a lever for actuating the mechanism for punching out the staples; and a housing for enclosing and connecting the magazine and the lever. An inner surface of the housing includes a linear positioning portion continuing from an opening of the housing, and a latching portion for latching the magazine, a surface of the magazine tangent to the inner surface of the housing includes a positioning portion conforming to the positioning portion of the housing, and a latching portion conforming to the latching portion of the housing, and combining the positioning portion of the housing and the positioning portion of the magazine, and fitting the latching portion of the housing and the latching portion of the magazine connect the housing and the magazine.

6 Claims, 5 Drawing Sheets

(56) References Cited

U.S. PATENT DOCUMENTS

| | | | | |
|---|---|---|---|---|
| 4,591,086 A * | 5/1986 | Campbell | A61B 17/0684 227/114 |
| 4,662,555 A * | 5/1987 | Thornton | A61B 17/0684 227/120 |
| 4,813,586 A * | 3/1989 | Seifert | A61B 17/0684 227/120 |
| 4,919,320 A * | 4/1990 | Storace | A61B 17/0684 227/116 |
| 5,908,149 A * | 6/1999 | Welch | A61B 17/0684 227/176.1 |
| 6,318,616 B1 * | 11/2001 | Pasqualucci | A61B 17/0684 227/156 |
| 2005/0143759 A1 * | 6/2005 | Kelly | A61B 17/072 606/139 |
| 2012/0325890 A1 * | 12/2012 | Matsutani | A61B 17/0684 227/176.1 |

* cited by examiner (a)

(b)

(c)

(d)

(a)

(b)

(c)

MEDICAL STAPLER

TECHNICAL FIELD

The present invention relates to a medical stapler, more specifically, a medical stapler allowing easy connection of a magazine and a housing during assembly.

BACKGROUND ART

In surgical procedures, a medical stapler may be used for suturing a living organism that has been cut open. A medical stapler disclosed in Patent Document 1 is constituted by a housing, a lever, which is rotatably attached to the housing, and a magazine, which is attached to the housing in a detachable manner and stores multiple staples. FIG. 6 illustrate a conventional medical stapler, wherein FIG. 6(a) is a side view of the entirety and FIG. 6(b) is a side view of a magazine. Note that while the conventional medical stapler 20 shown in FIG. 6(a) has a lever 3 rotatably attached to a housing 1, there are staplers having the magazine 2 and the lever 3 connected rotatably and attached to the housing 1.

The magazine 2 includes an anvil, which is formed by making a front edge of a rail secured in the magazine 2 thin and bending it, a ram, which is arranged in a movable manner to and back from the front edge of the anvil, and a biasing member, which biases the ram in a direction away from the front edge of the anvil. A predetermined number of staples are aligned on the rail, and these staples are then biased by an elastic member toward the anvil at the edge of the rail.

The staples are formed by bending a rounded, stainless-steel wire rod into a U shape, and are formed having pointed legs so as to reduce resistance when both end portions pierce through a living organism. By applying pressure on the lever 3, the ram is driven and lowered by the lever 3 so that the edge of the ram makes contact with the staples held on the anvil. If pressure is further applied on the lever 3 to lower the ram, the staples are bent into a quadrangular shape, so that they can suture a living organism.

The housing 1 and the lever 3 are made of synthetic resin, such as ABS resin, and formed into shapes in consideration of gripping ease and user-friendliness. Moreover, the magazine 2 is generally formed using transparent ABS resin, which allows external confirmation of the remaining number of the staples stored therewithin.

Connection of the magazine 2 and the housing 1 of such a conventional stapler 20 is established by fitting together a latching convexity 2b provided in the magazine 2 and a latching concavity 1b provided in the housing 1. Here, the conventional latching concavity 1b and latching convexity 2b have linear shapes as illustrated and are provided in parallel along the length of the rail on which the staples are deployed.

Since if the connection between the housing 1 and the magazine 2 loosens, they may easily disconnect from each other, thickness of the magazine 2 is formed so as to settle perfectly within the width between the inner surfaces of the housing 1, thereby further increasing rigidity of the housing 1. As a result, the latching convexity 2b projects out from the width between the inner surfaces of the housing 1, and thus connection between the housing 1 and the magazine 2 is not easy. Moreover, in order to reduce instability after assembly, the conventional latching concavity 1b and latching convexity 2b are fit together with a minimum gap therebetween, and while having a certain length is preferred, if they are too long, connection becomes even more difficult.

PRIOR ART DOCUMENTS

Patent Documents

Patent Document 1: JP 2006-305136 A

DISCLOSURE OF INVENTION

Problem to be Solved by the Invention

If connection between a housing and a magazine as in the conventional case is difficult, assembly takes a long time, and manufacture efficiency is low, leading to increase in cost.

In light of these conditions, the present invention aims to provide a medical stapler assembled securely, while allowing easy connection between magazine and house.

Means of Solving the Problem

A medical stapler according to the present invention is characterized in that it includes a magazine including staples, a rail for aligning the staples, and a mechanism for punching out the staples; a lever for actuating the mechanism for punching out the staples; and a housing for enclosing and connecting the magazine and the lever. An inner surface of the housing comprises a linear positioning portion continuing from an opening of the housing, and a latching portion for latching the magazine, and a surface of the magazine tangent to the inner surface of the housing includes a positioning portion in accordance with form of the positioning portion of the housing. A latching portion in accordance with form of the latching portion of the housing, and combining the positioning portion of the housing and the positioning portion of the magazine, and fitting the latching portion of the housing and the latching portion of the magazine connect the housing and the magazine.

Here, it is possible that: the inner surface of the housing further comprises a linear groove-shaped positioning concavity as a positioning portion continuing from an opening of the housing, and a latching concavity as a latching portion for latching the magazine; the surface of the magazine tangent to the inner surface of the housing further includes a positioning convexity in accordance with the form of the positioning concavity, and a latching convexity in accordance with the form of the latching concavity; the latching convexity is shorter than the positioning convexity and has a linear form facing a different direction than the positioning convexity; and a tilt angle of the positioning convexity and the latching convexity on acute angle sides along the length of the rail is 15 to 75 degrees.

Alternatively, it is also possible that the inner surface of the housing comprises an auxiliary concavity at a position where the latching convexity and the opening of the housing make contact for fitting the latching convexity and the latching concavity; the auxiliary concavity has a depth in which the latching convexity settles at the position of the opening of the housing, and has a tilted surface that becomes shallower as it approaches the latching concavity; and the latching convexity has a tilted surface at the front portion in the moving direction.

Result of the Invention

The medical stapler according to the present invention provides an excellent result of improving manufacture efficiency of the medical stapler since connection between magazine and housing is easy.

BRIEF DESCRIPTION OF DRAWINGS

FIG. 1(a) is a top view, FIG. 1(b) is a side view, and FIG. 1(c) is a front view;

FIG. 2(a) is a lateral cross-sectional view and FIG. 2(b) is a bottom view;

FIG. 5(a) is an embodiment illustrated in FIGS. 1 to 3, FIG. 5(b) is an embodiment of the case where positions of positioning portions and latching portions are reversed, and FIG. 5(c) is an embodiment where the latching portion is circular; FIG. 6(a) is a side view of the entirety and FIG. 6(b) is a side view of a magazine.

BEST MODE FOR CARRYING OUT THE INVENTION

Embodiments of the present invention are described while referencing the attached drawings.

Figure 1:
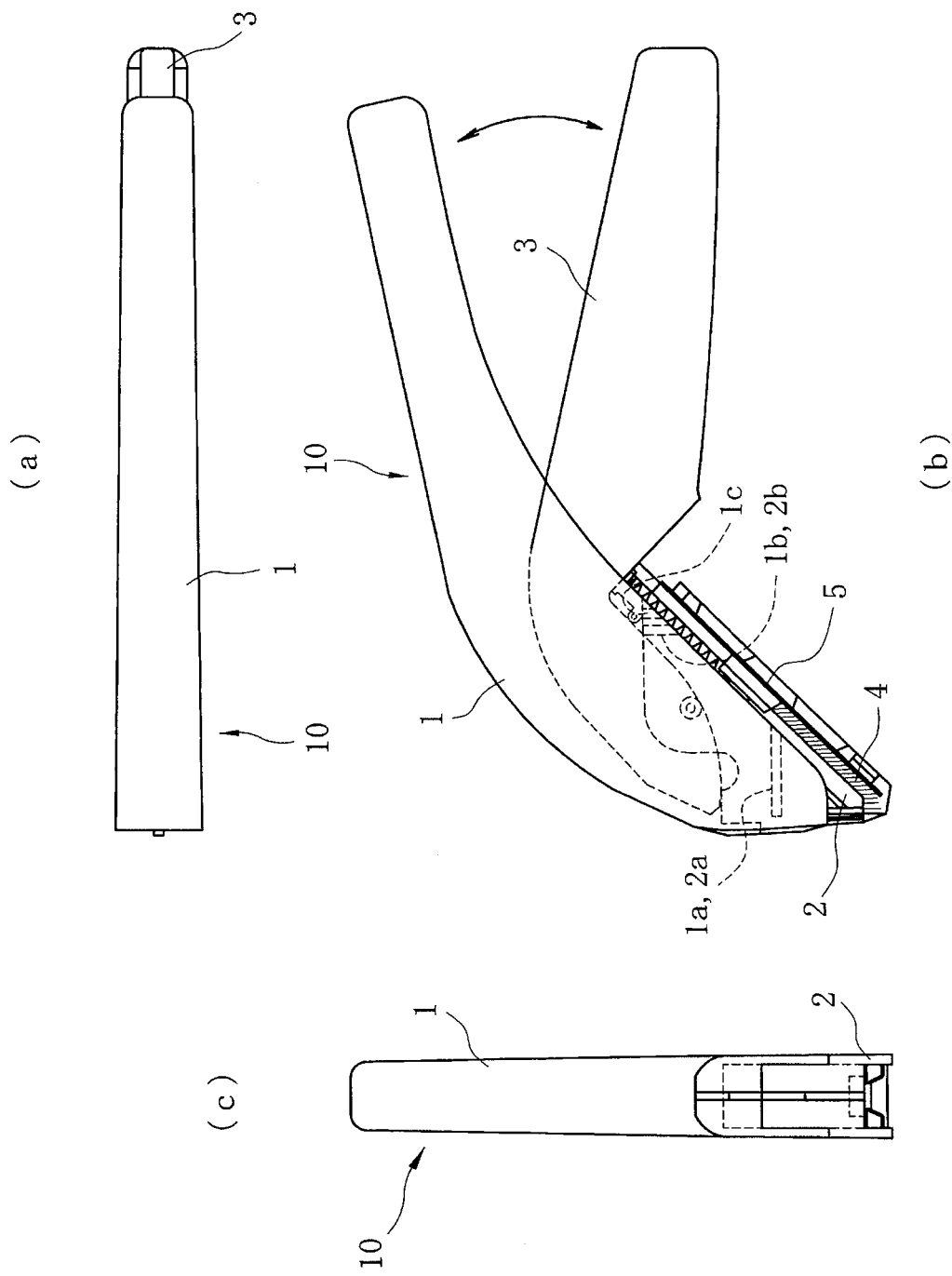
FIG. 1 show three views of a medical stapler, where

FIG. 1 show three views of a medical stapler of the present invention, where FIG. 1(a) is a top view, FIG. 1(b) is a side view, and FIG. 1(c) is a front view. A medical stapler 10 is roughly constituted by a magazine 2, a lever 3, and a housing 1.

The housing 1 encloses the magazine 2 and the lever 3 from the sides, joining into a unified body. Moreover, a part of the housing 1 is a handling portion of the medical stapler 10, and is grasped along with the lever 3 so as to punch out a staple 4.

The magazine 2 includes therewithin multiple staples 4, a rail 5 for aligning the staples, and a mechanism of punching out a staple. The mechanism of punching out a staple sutures an affected area of the body by bending the U-shaped staple 4 into a quadrangular shape when the lever 3 is grasped.

Figure 2:
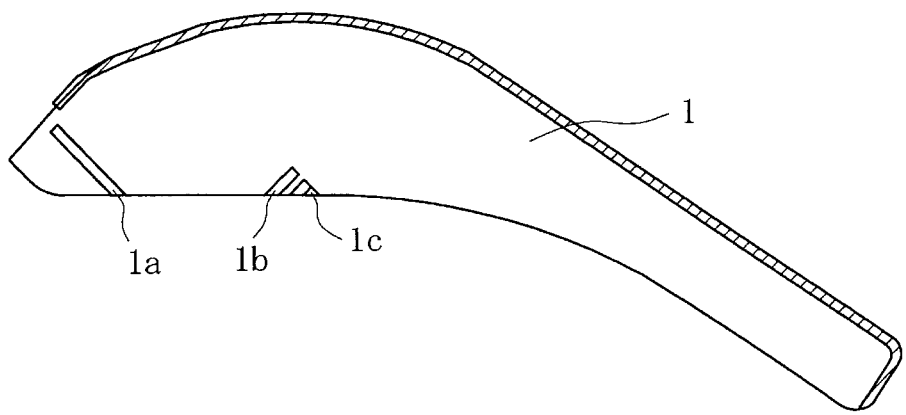
FIG. 2 illustrate a housing, where
Figure 2:
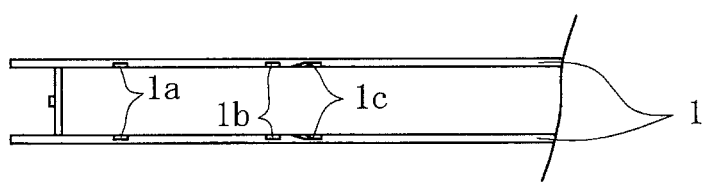
Figure 3:
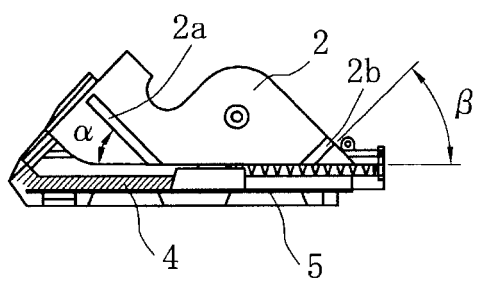
FIG. 3 is a side view of a magazine.

FIG. 2 illustrate the housing, where FIG. 2(a) is a lateral cross-sectional view and FIG. 2(b) is a bottom view. FIG. 3 is a side view of the magazine. A positioning concavity 1a and a latching concavity 1b are provided in an inner surface of the housing 1, and matching positioning convexity 2a and latching convexity 2b are provided in the surface of the magazine 2 tangent to the inner surface of the housing 1. Moreover, an auxiliary concavity 1c may be provided in the housing 1 as well. Note that these concavities and convexities may be provided on either surface enclosing the magazine 2, or they may be provided on a single surface as long as rigidity of the housing 1 and the magazine 2 is high and do not easily disconnect from each other.

The positioning concavity 1a has a linear groove form, continuing from an opening of the housing 1, and the positioning convexity 2a provided in the magazine 2 is inserted from the opening side, where these function as a guide for connecting the housing 1 and the magazine 2. Furthermore, when the connection is made, resulting in a completed form, they function as a latching member.

The latching concavity 1b fits into the latching convexity 2b so as to connect the housing 1 and the magazine 2. When making the form of the latching convexity 2b into a linear form, it should be shorter than the positioning convexity 2a and facing in a different direction. This is because if it is longer than the positioning convexity 2a, the latching convexity 2b makes contact with the housing 1 first, preventing insertion of the positioning convexity 2a into the positioning concavity 1a. Furthermore, when the latching convexity 2b and the positioning convexity 2a are parallel, the magazine 2 may be easily detached from the housing 1 if it is moved in that direction, thereby needing to face in another direction. Note that it is preferable that tilt angles α and β, which are on acute angle sides along the length of the rail on which the staples 4 are deployed, are 15 to 75 degrees for the positioning convexity 2a and the latching convexity 2b, and a crossing angle when the positioning convexity 2a and the latching convexity 2b are virtually extended is 30 to 135 degrees. This is because there is an advantage that deploying the convexities at angles close to right angles in the direction that the staples 4 are punched out is preferable in light of reduction in instability, and if the positioning convexity 2a and the latching convexity 2b stand almost perpendicular to each other, when a force acts along the length of one, the other can resist along the entire straight line.

With such positioning concavity 1a and positioning convexity 2a, and latching concavity 1b and latching convexity 2b, since both of the concavities and convexities fit together, it makes a structure that does not easily disconnect. Conventionally, since the fitting concavity and convexity are in only one place, it becomes unstable without a certain length, and thus has a problem that fitting becomes difficult when the concavity and convexity are lengthened. Correspondingly, with the present invention, fitting is not difficult even if the positioning convexity 2a is lengthened, and thus may be made sufficiently long, as well as have a secure connection.

Alternatively, an auxiliary concavity 1c may be provided at a position in the inner surface of the housing 1 making contact of the latching convexity 2b with the opening of the housing 1 for further facilitating fitting. That is, the auxiliary concavity 1c is a convexity provided for facilitating insertion of the latching convexity 2b into the housing 1.

Figure 4:
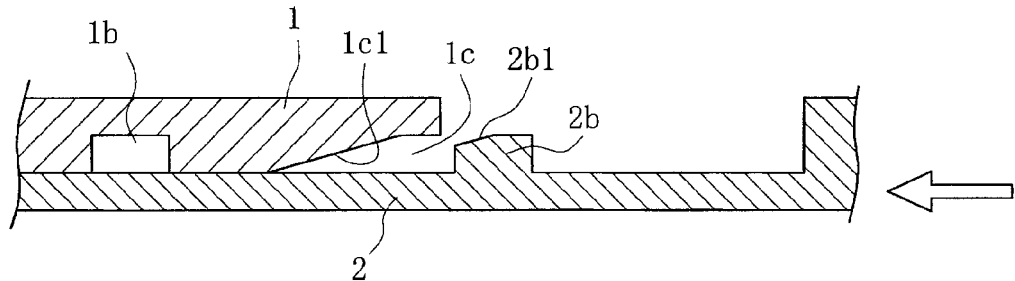
FIGS. 4(a) to 4(d) are diagrams for describing how to fit using an auxiliary concavity.
Figure 4:
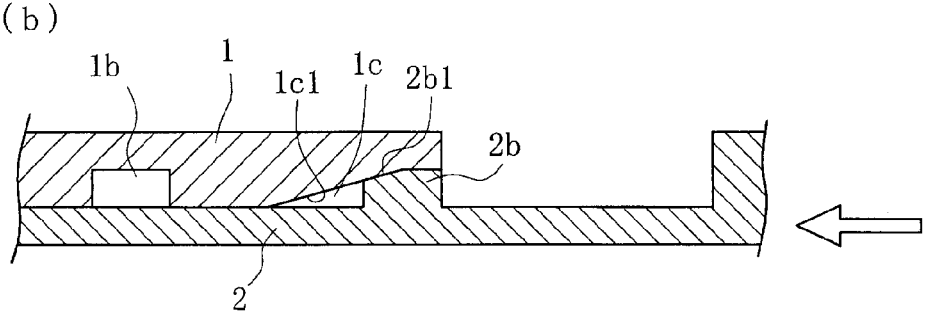
Figure 4:
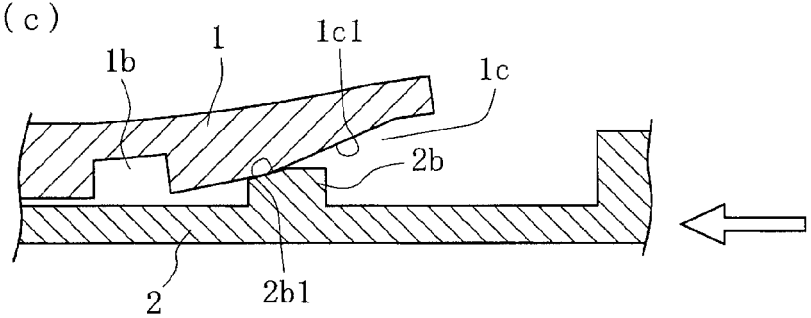
Figure 4:
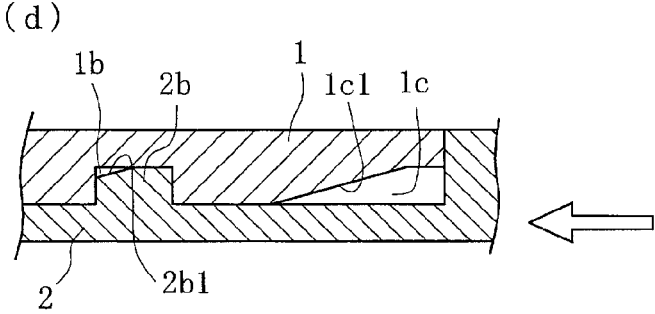

FIGS. 4(a) to 4(d) are diagrams describing how to fit using the auxiliary concavity 1c. FIG. 4(a) shows a state of sliding the magazine 2 while the inner surface of the housing 1 is making contact with the surface of the magazine 2. Here, the auxiliary concavity 1c has a depth in which the latching convexity 2b can be settled when it is positioned at the opening of the housing 1, and has a tilted surface 1c1, which becomes shallower as it approaches the latching concavity 1b. Moreover, the latching convexity 2b has a tilted surface 2b1 at the front portion in the moving direction. FIG. 4(b) is a state where the latching convexity 2b settles perfectly in the auxiliary concavity 1c. Furthermore, when the magazine 2 is pushed in from here, the housing 1 is deformed, as shown in FIG. 4(c). The tilted surface 1c1 of the auxiliary concavity and tilted surface 2b1 of the latching convexity are useful for smoother fitting, and especially since a tilted surface is provided to both portions, each of the tilted surfaces can function more effectively, as illustrated in the drawings. When the magazine 2 is further pushed in, the latching convexity 2b is settled in the latching concavity 1b, as shown in FIG. 4(d). Since there is no tilted surface in the direction pulling out the magazine 2 in this case, it is made difficult to disconnect.

Figure 5:
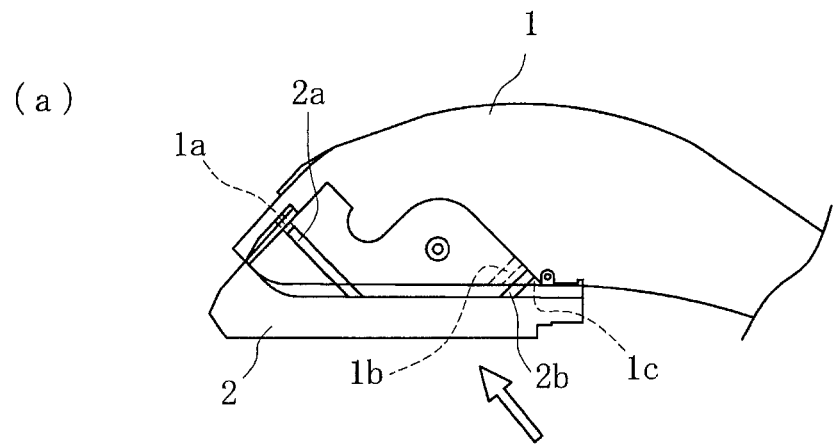
FIG. 5 are side views of embodiments illustrating how to connect the housing and the magazine, where
Figure 5:
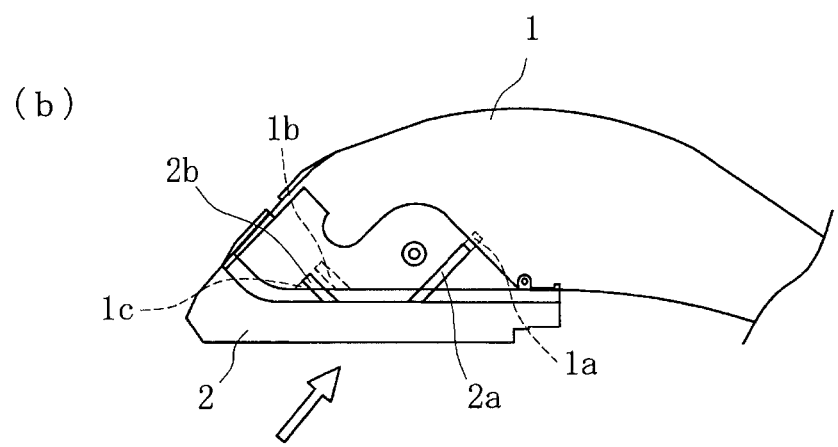
Figure 5:
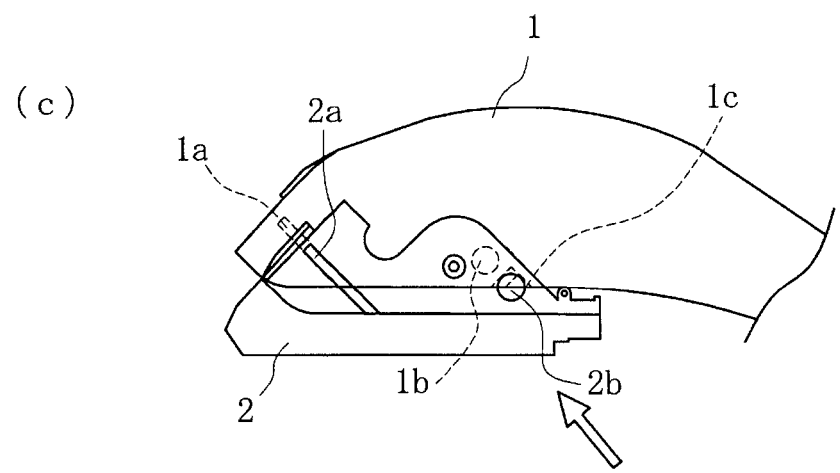
Figure 6:
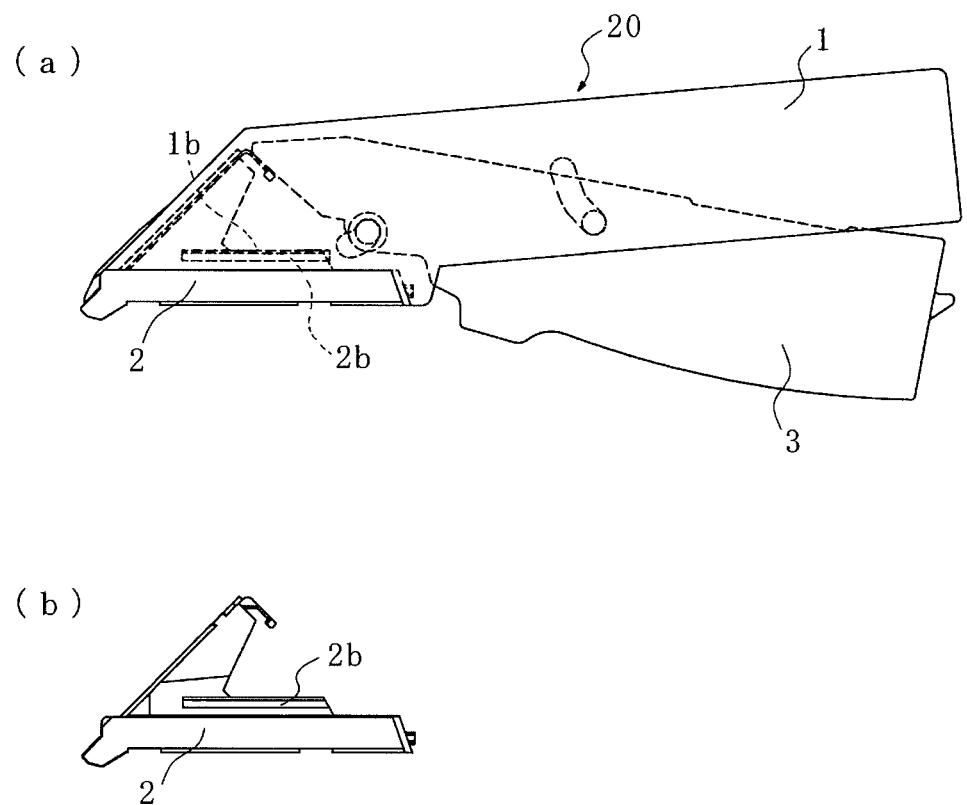
FIG. 6 illustrate a conventional medical stapler, where

FIG. 5 are side views of embodiments illustrating states of connecting the housing 1 and the magazine 2, where FIG. 5(a) is the embodiment illustrated in FIGS. 1 to 3, FIG. 5(b) is an embodiment of the case where positions of positioning portions and latching portions are reversed, and FIG. 5(c) is an embodiment where the latching portion is circular.

When the side from which the staples 4 of the magazine 2 are punched out is set as the front side of the magazine 2, FIG. 5(a) is an example where the positioning concavity 1a and the positioning convexity 2a are provided on the front side, and the latching concavity 1b and the latching convexity 2b are provided on the back side. FIG. 5(b) is the reverse of FIG. 5(a), where the latching concavity 1b and the latching convexity 2b are provided on the front side of the magazine 2, and the positioning concavity 1a and the positioning convexity 2a are provided on the back side. At this time, since the magazine 2 moves along the length of the positioning concavity 1a to connect, direction of pushing the magazine 2 in FIG. 5a is different from the same in FIG. 5b. Moreover, it is possible to make an acute angle side of a tilt angle against the length of the rail opposite that of FIGS. 5a and 5b, and directions of the positioning concavity 1a and the positioning convexity 2a, and the latching concavity 1b and the latching convexity 2b mutually face inward. The direction of pushing the magazine 2 also differs in this case as well. In this manner, the direction of pushing the magazine 2 is determined according to directions of the positioning concavity 1a and the positioning convexity 2a.

FIG. 5(c) is an example where forms of the latching concavity 1b and the latching convexity 2b are circular. As such, the forms of the latching concavity 1b and the latching convexity 2b are not particularly limited to linear forms if they can be fitted securely, and may be circular or another form.

Moreover, while the positioning convexity 2a and the latching convexity 2b are provided to the magazine 2 and the positioning concavity 1a, the latching concavity 1b, and the auxiliary concavity 1c are provided in the housing 1 in this embodiment, needless to say a configuration in which the concavities and convexities are reversed, providing the positioning convexity 2a and the latching convexity 2b to the housing 1 and the positioning concavity 1a, the latching concavity 1b, and the auxiliary concavity 1c to the magazine 2 is possible.

DESCRIPTION OF REFERENCE NUMERALS 1 housing
1a positioning concavity
1b latching concavity
1c auxiliary concavity
1c1 tilted surface of auxiliary concavity
2 magazine
2a positioning convexity
2b latching convexity
2b1 tilted surface of latching convexity
3 lever
4 staple
5 rail
10, 20 medical stapler

The invention claimed is:

1. A medical stapler, comprising:
   a magazine that comprises staples, a rail for aligning staples, and a mechanism for punching out the staples;
   a lever for actuating the mechanism for punching out the staples; and
   a housing for enclosing and connecting the magazine and the lever, wherein
   an inner surface of the housing comprises a linear positioning portion continuing from an opening of the housing, and a latching portion for latching the magazine; and
   a surface of the magazine tangent to the inner surface of the housing comprises a positioning portion in accordance with form of the positioning portion of the housing, and a latching portion in accordance with form of the latching portion of the housing, and
   combining the positioning portion of the housing and the positioning portion of the magazine to form a guide for fitting together the latching portion of the housing and the latching portion of the magazine to connect the housing and the magazine,
   wherein the inner surface of the housing further comprises a linear groove-shaped positioning concavity as a positioning portion continuing from an opening of the housing, and a latching concavity as a latching portion for latching the magazine, and
   the surface of the magazine tangent to the inner surface of the housing further comprises a positioning convexity in accordance with the form of the positioning concavity, and a latching convexity in accordance with the form of the latching concavity.

2. The medical stapler according to claim 1, wherein the latching convexity is shorter than the positioning convexity and has a linear form facing a different direction than the positioning convexity.

3. The medical stapler according to claim 2, wherein a tilt angle of the positioning convexity and the latching convexity on acute angle sides along the length of the rail is 15 to 75 degrees.

4. The medical stapler according to claim 1, wherein the inner surface of the housing comprises an auxiliary concavity at a position where the latching convexity and the opening of the housing make contact for fitting the latching convexity and the latching concavity, and
   the auxiliary concavity has a depth in which the latching convexity settles at the position of the opening of the housing, and has a tilted surface that becomes shallower as it approaches the latching concavity.

5. The medical stapler according to claim 1, wherein the latching convexity has a tilted surface at the front portion thereof in a direction in which the magazine is slid into the housing.

6. A medical stapler, comprising:
   a magazine that comprises staples, a rail for aligning staples, and a mechanism for punching out the staples;
   a lever for actuating the mechanism for punching out the staples; and
   a housing for enclosing and connecting the magazine and the lever, wherein
   an inner surface of the housing comprises a linear positioning portion continuing from an opening of the housing, and a latching portion for latching the magazine; and
   a surface of the magazine tangent to the inner surface of the housing comprises a positioning portion in accordance with form of the positioning portion of the housing, and a latching portion in accordance with form of the latching portion of the housing, and
   combining the positioning portion of the housing and the positioning portion of the magazine to form a guide for fitting together the latching portion of the housing and the latching portion of the magazine to connect the housing and the magazine,
   wherein the surface of the magazine tangent to the inner surface of the housing comprises a linear groove-shaped positioning concavity as a positioning portion, and a latching concavity as a latching portion for latching the housing,
   wherein the inner surface of the housing further comprises further comprises a positioning convexity conforming to the form of the positioning concavity, and a latching convexity conforming to the form of the latching concavity.

* * * * *